(12) United States Patent
Korth et al.

(10) Patent No.: US 6,995,280 B2
(45) Date of Patent: Feb. 7, 2006

US006995280B2

(54) PROCESS FOR PREPARING (MERCAPTOORGANYL)ALKOXYSILANES

(75) Inventors: Karsten Korth, Grenzach-Wyhlen (DE); Philipp Albert, Lörrach (DE); Ingo Kiefer, Schopfheim (DE)

(73) Assignee: Degussa AG, Düsseldorf (DE)

( * ) Notice: Subject to any disclaimer, the term of this patent is extended or adjusted under 35 U.S.C. 154(b) by 4 days.

(21) Appl. No.: 10/980,861

(22) Filed: Nov. 4, 2004

(65) Prior Publication Data
US 2005/0124821 A1    Jun. 9, 2005

(30) Foreign Application Priority Data
Nov. 6, 2003 (DE) ................................ 103 51 735

(51) Int. Cl.
*C07F 7/04*    (2006.01)

(52) U.S. Cl. ..................................................... 556/429

(58) Field of Classification Search ................. 556/429
See application file for complete search history.

(56) References Cited

U.S. PATENT DOCUMENTS

| 3,590,065 A | 6/1971 | Rakus et al. .......... 260/448.8 R |
| 3,849,471 A | 11/1974 | Omietanski et al. .. 260/448.2 E |
| 4,012,403 A | 3/1977 | Mui ..................... 260/448.8 R |
| 4,082,790 A | 4/1978 | Speier ................. 260/448.8 E |
| 5,107,009 A | 4/1992 | Rauleder et al. ............ 556/429 |
| 5,840,952 A | 11/1998 | Kudo et al. ................. 556/429 |

FOREIGN PATENT DOCUMENTS

| DE | 2035 619 | 2/1971 |
| EP | 0 018 094 B1 | 6/1982 |
| EP | 0 471 164 B1 | 11/1995 |
| GB | 1102251 | 2/1968 |

OTHER PUBLICATIONS

Abstract for Reference B2 above.
Abstract for Reference B3 above.

*Primary Examiner*—Samuel Barts
(74) *Attorney, Agent, or Firm*—Michael A. Sanzo; Fitch, Even, Tabin & Flannery

(57) ABSTRACT

The present invention is directed to a process for preparing (mercaptoorganyl)alkoxysilanes by conversion of alkali-metal hydrogensulfide with a mixture of (haloorganyl)alkoxysilane and (haloorganyl)halosilane in an alcohol with air excluded and at an elevated pressure.

10 Claims, No Drawings

PROCESS FOR PREPARING (MERCAPTOORGANYL)ALKOXYSILANES

CROSS REFERENCE TO RELATED APPLICATIONS

The present application claims priority to German application DE 103 51 735.9, filed on Nov. 6, 2003, the contents of which is hereby incorporated by reference.

FIELD OF THE INVENTION

The present invention relates to a process for preparing (mercaptoorganyl)alkoxysilanes.

BACKGROUND OF THE INVENTION

Although there are several processes available for producing (mercaptoalkyl)alkoxysilanes, each has significant limitations. In one process, alkali hydrogen sulfides are reacted with (haloalkyl)alkoxysilanes in methanolic medium at normal pressure to produce the corresponding (mercaptoalkyl)alkoxysilanes (GB 1 102 251). However, this procedure requires an unusually long reaction-time (96 h) to achieve a high rate of conversion and typically results in a poor yield.

As an alternative, (mercaptoalkyl)alkoxysilanes may be produced by reacting alkali hydrogen sulfide with suitable (haloalkyl)alkoxysilanes in the presence of a 10–100% molar excess of $H_2S$ (U.S. Pat. No. 5,840,952). However, on an industrial scale, this process has the disadvantage that highly toxic $H_2S$ has to be stored, metered and handled. In addition, the process is carried out in two stages and this results in a diminished space-time yield.

Another process for preparing (mercaptoalkyl)alkoxysilanes is by converting (haloalkyl)alkoxysilanes with alkali hydrogensulfide (NaSH) in polar, aprotic solvents (EP 0 471 164). A drawback of this process is that it uses a large quantity, at least 50 vol. %, of solvent, and this may be highly toxic, e.g., dimethylformamide. In addition, the high boiling-point of solvents such as dimethylformamide makes distillative reprocessing and purification of the reaction products more difficult.

DESCRIPTION OF THE INVENTION

The present invention is directed to a process for preparing (mercaptoorganyl)alkoxysilanes, that avoids the use of highly toxic hydrogensulfide or dimethylformamide, and that enables short reaction-times, high space-time yields and good selectivity. The process involves reacting an alkali metal hydrogen sulfide with a mixture of (haloorganyl)alkoxy-silane and (haloorganyl)halosilane in an alcohol with the exclusion of air and under elevated pressure. The term "under elevated pressure" means an excess pressure of from 0.1 to 10 bar, and preferably from 1 to 7 bar, above normal pressure.

The (mercaptoorganyl)alkoxysilanes made by the process include compounds of the general formula I:

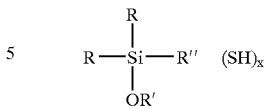

wherein:
the substituents R are identical or different and are: a $C_1$–$C_8$ alkyl (preferably $CH_3$); an alkenyl (preferably a $C_2$–$C_{12}$ alkenyl); an aryl (preferably a $C_6$–$C_{10}$ aryl); an aralkyl (preferably a $C_7$–$C_{16}$ aralkyl); or a group OR';
the substituents R' are identical or different and are: a $C_1$–$C_{24}$ (preferably $C_1$–$C_4$ or $C_{12}$–$C_{18}$) branched or unbranched monovalent alkyl or alkenyl group; an aryl group (preferably a $C_6$–$C_{10}$ aryl group), or an aralkyl group (preferably a $C_7$–$C_{16}$ aralkyl group);
R" is a branched or unbranched, saturated or unsaturated, aliphatic, aromatic or mixed aliphatic/aromatic divalent $C_1$–$C_{30}$ hydrocarbon group which is optionally substituted by F, Cl, Br, I, $NH_2$ or NHR'; and
x is equal to 1–3.

When x=1, R" is preferably —$CH_2$—, —$CH_2CH_2$—, —$CH_2CH_2CH_2$—, —$CH_2CH_2CH_2CH_2$—, —$CH(CH_3)$—, —$CH_2CH(CH_3)$—, —$CH(CH_3)CH_2$—, —$C(CH_3)_2$—, —$CH(C_2H_5)$—, —$CH_2CH_2CH(CH_3)$—, —$CH_2CH(CH_3)CH_2$—, or

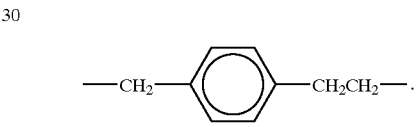

When x=2, R" is preferably CH, —CH—$CH_2$, —$CH_2$—CH, C—$CH_3$, —CH—$CH_2$—$CH_2$, —CH—CH—$CH_3$, or —$CH_2$—CH—$CH_2$.

Preferred (mercaptoorganyl)alkoxysilanes of formula I are:
3-mercaptopropyl(trimethoxysilane);
3-mercaptopropyl(triethoxysilane);
3-mercaptopropyl(diethoxymethoxysilane);
3-mercaptopropyl(tripropoxysilane);
3-mercaptopropyl(dipropoxymethoxysilane);
3-mercaptopropyl(tridodecanoxysilane);
3-mercaptopropyl(tritetradecanoxysilane);
3-mercaptopropyl(trihexadecanoxysilane);
3-mercaptopropyl(trioctadecanoxysilane);
3-mercaptopropyl(didodecanoxy)tetradecanoxysilane;
3-mercaptopropyl(dodecanoxy)tetradecanoxy(hexadecanoxy)silane;
3-mercaptopropyl(dimethoxymethylsilane);
3-mercaptopropyl(methoxydimethylsilane);
3-mercaptopropyl(diethoxymethylsilane);
3-mercaptopropyl(ethoxydimethylsilane);
3-mercaptopropyl(dipropoxymethylsilane);
3-mercaptopropyl(propoxydimethylsilane);
3-mercaptopropyl(diisopropoxymethylsilane);
3-mercaptopropyl(isopropoxydimethylsilane);
3-mercaptopropyl(dibutoxymethylsilane);
3-mercaptopropyl(butoxydimethylsilane);
3-mercaptopropyl(diisobutoxymethylsilane);
3-mercaptopropyl(isobutoxydimethylsilane);
3-mercaptopropyl(didodecanoxymethylsilane);
3-mercaptopropyl(dodecanoxydimethylsilane);

3-mercaptopropyl(ditetradecanoxymethylsilane);
3-mercaptopropyl(tetradecanoxydimethylsilane);
2-mercaptoethyl(trimethoxysilane);
2-mercaptoethyl(triethoxysilane);
2-mercaptoethyl(diethoxymethoxysilane);
2-mercaptoethyl(tripropoxysilane);
2-mercaptoethyl(dipropoxymethoxysilane);
2-mercaptoethyl(tridodecanoxysilane);
2-mercaptoethyl(tritetradecanoxysilane);
2-mercaptoethyl(trihexadecanoxysilane);
2-mercaptoethyl(trioctadecanoxysilane);
2-mercaptoethyl(didodecanoxy)tetradecanoxysilane;
2-mercaptoethyl(dodecanoxy)tetradecanoxy(hexadecanoxy)silane;
2-mercaptoethyl(dimethoxymethylsilane);
2-mercaptoethyl(methoxydimethylsilane);
2-mercaptoethyl(diethoxymethylsilane);
2-mercaptoethyl(ethoxydimethylsilane);
1-mercaptomethyl(trimethoxysilane);
1-mercaptomethyl(triethoxysilane);
1-mercaptomethyl(diethoxymethoxysilane);
1-mercaptomethyl(dipropoxymethoxysilane);
1-mercaptomethyl(tripropoxysilane);
1-mercaptomethyl(trimethoxysilane);
1-mercaptomethyl(dimethoxymethylsilane);
1-mercaptomethyl(methoxydimethylsilane);
1-mercaptomethyl(diethoxymethylsilane);
1-mercaptomethyl(ethoxydimethylsilane);
1,3-dimercaptopropyl(trimethoxysilane);
1,3-dimercaptopropyl(triethoxysilane);
1,3-dimercaptopropyl(tripropoxysilane);
1,3-dimercaptopropyl(tridodecanoxysilane);
1,3-dimercaptopropyl(tritetradecanoxysilane);
1,3-dimercaptopropyl(trihexadecanoxysilane);
2,3-dimercaptopropyl(trimethoxysilane);
2,3-dimercaptopropyl(triethoxysilane);
2,3-dimercaptopropyl(tripropoxysilane);
2,3-dimercaptopropyl(tridodecanoxysilane);
2,3-dimercaptopropyl(tritetradecanoxysilane);
2,3-dimercaptopropyl(trihexadecanoxysilane);
3-mercaptobutyl(trimethoxysilane);
3-mercaptobutyl(triethoxysilane);
3-mercaptobutyl(diethoxymethoxysilane);
3-mercaptobutyl(tripropoxysilane);
3-mercaptobutyl(dipropoxymethoxysilane);
3-mercaptobutyl(dimethoxymethylsilane);
3-mercaptobutyl(diethoxymethylsilane);
3-mercapto-(2-methyl)propyl(dimethylmethoxysilane);
3-mercapto-2-methylpropyl(dimethylethoxysilane);
3-mercapto-2-methylpropyl(dimethyltetradecanoxysilane);
3-mercaptobutyl(dimethylmethoxysilane);
3-mercapto-2-methylpropyl(dimethylethoxysilane);
3-mercapto-(2-methyl)propyl(dimethylmethoxysilane);
3-mercapto-2-methylpropyl(dimethyltetradecanoxysilane);
3-mercaptobutyl(dimethylethoxysilane);
3-mercaptobutyl(tridodecanoxysilane);
3-mercaptobutyl(tritetradecanoxysilane);
3-mercaptobutyl(trihexadecanoxysilane);
3-mercaptobutyl(didodecanoxy)tetradecanoxysilane; or
3-mercaptobutyl(dodecanoxy)tetradecanoxy(hexadecanoxy) silane.

These compounds and others of formula I may be produced individually or mixtures of the compounds may be produced.

The (haloorganyl)alkoxysilanes compounds used in the process include those of general formula II:

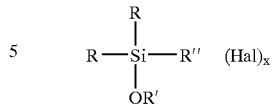

wherein x, R, R' and R" are as defined above and Hal is chlorine, bromine, fluorine or iodine. Preferred (haloorganyl)alkoxysilanes are:
3-chlorobutyl(triethoxysilane);
3-chlorobutyl(trimethoxysilane);
3-chlorobutyl(diethoxymethoxysilane);
3-chloropropyl(triethoxysilane);
3-chloropropyl(trimethoxysilane);
3-chloropropyl(diethoxymethoxysilane);
2-chloroethyl(triethoxysilane);
2-chloroethyl(trimethoxysilane);
2-chloroethyl(diethoxymethoxysilane);
1-chloromethyl(triethoxysilane);
1-chloromethyl(trimethoxysilane);
1-chloromethyl(diethoxymethoxysilane);
3-chloropropyl(diethoxymethylsilane);
3-chloropropyl(dimethoxymethylsilane);
2-chloroethyl(diethoxymethylsilane);
2-chloroethyl(dimethoxymethylsilane);
1-chloromethyl(diethoxymethylsilane);
1-chloromethyl(dimethoxymethylsilane);
3-chloropropyl(ethoxydimethylsilane);
3-chloropropyl(methoxydimethylsilane);
2-chloroethyl(ethoxydimethylsilane);
2-chloroethyl(methoxydimethylsilane);
1-chloromethyl(ethoxydimethylsilane); or
1-chloromethyl(methoxydimethylsilane).

The (haloorganyl)alkoxysilane may be a single compound of the general formula II or a mixture of compounds of the general formula II.

The (haloorganyl)halosilanes used in the process include compounds of the general formula III:

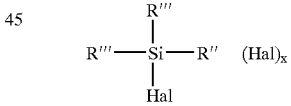

wherein x, Hal, R" and R" are as defined above and the substituents R''', independently of one another, are R or Hal. Preferred (haloorganyl)halosilanes are:
3-chlorobutyl(trichlorosilane);
3-chloropropyl(trichlorosilane);
2-chloroethyl(trichlorosilane);
1-chloromethyl(trichlorosilane);
3-chlorobutyl(dichloromethoxysilane);
3-chloropropyl(dichloromethoxysilane);
2-chloroethyl(dichloromethoxysilane);
1-chloromethyl(dichloromethoxysilane);
3-chlorobutyl(dichloroethoxysilane);
3-chloropropyl(dichloroethoxysilane);
2-chloroethyl(dichloroethoxysilane);
1-chloromethyl(dichloroethoxysilane);
3-chlorobutyl(chlorodiethoxysilane);
3-chloropropyl(chlorodiethoxysilane);

2-chloroethyl(chlorodiethoxysilane);
1-chloromethyl(chlorodiethoxysilane);
3-chlorobutyl(chlorodimethoxysilane);
3-chloropropyl(chlorodimethoxysilane);
2-chloroethyl(chlorodimethoxysilane);
1-chloromethyl(chlorodimethoxysilane);
3-chlorobutyl(dichloromethylsilane);
3-chloropropyl(dichloromethylsilane);
2-chloroethyl(dichloromethylsilane);
1-chloromethyl(dichloromethylsilane);
3-chlorobutyl(chloro)(methyl)methoxysilane;
3-chloropropyl(chloro)(methyl)methoxysilane;
2-chloroethyl(chloro)(methyl)methoxysilane;
1-chloromethyl(chloro)(methyl)methoxysilane;
3-chlorobutyl(chloro)(methyl)ethoxysilane;
3-chloropropyl(chloro)(methyl)ethoxysilane;
2-chloroethyl(chloro)(methyl)ethoxysilane;
1-chloromethyl(chloro)(methyl)ethoxysilane;
3-chlorobutyl(chlorodimethylsilane);
3-chloropropyl(chlorodimethylsilane);
2-chloroethyl(chlorodimethylsilane); or
1-chloromethyl(chlorodimethylsilane).

The (haloorganyl)halosilane used in the process may be a single compound of formula III or a mixture of compounds of formula III.

(Mercaptoorganyl)alkoxysilanes of the general formula I:

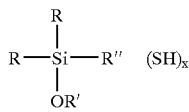

I can be prepared by reacting alkali-metal hydrogensulfide with (haloorganyl)alkoxysilanes of the general formula II:

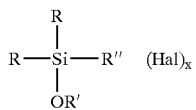

II and (haloorganyl)halosilane of the general formula III:

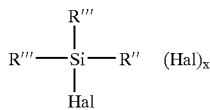

III in an alcohol in a closed vessel with air excluded and at an elevated pressure. The mixture of compounds produced by the process is determined by the choice of the (haloorganyl) alkoxysilanes and (haloorganyl)halosilanes. (Haloorganyl) alkyoxysilane and (haloorganyl)halosilane may be employed in a molar ratio of 1:0.00001 to 1:0.8, preferably in a molar ratio of 1:0.00001 to 1:0.5, and more preferentially in a molar ratio of 1:0.00001 to 1:0.09.

The mixture of the appropriate (haloorganyl)alkoxysilane and (haloorganyl)halosilane used for the process can be prepared before the addition of the alkali sulfide, depending on the apparatus used and the desired effect, for example selectivity of the reaction, duration of the reaction, reactor coating, reactor material or process sequence.

The quality and nature of the composition of the mixture of (haloorganyl)alkoxysilane and (haloorganyl)halosilane can be evaluated on the basis of the amount and nature of the hydrolysable Si-Hal bonds contained in the mixture. The quantity of hydrolysable Si halide in the mixture of (haloorganyl)alkyoxysilane and (haloorganyl)halosilane may amount to between 10 mg/kg and 800,000 mg/kg. This can be determined by adding 80 ml of ethanol and 10 ml of acetic acid to not more than 20 g of sample in a 150 ml glass beaker. The halide content is titrated potentiographically with a silver nitrate solution (c(AgNO3)=0.01 mol/l).

The optimum molar ratio of the mixture of (haloorganyl) alkoxysilanes and (haloorganyl)halosilanes depends, inter alia, on the number of Si-halogen functional groups of the chosen (haloorganyl)halosilanes. For example, in the reaction of 3-chloropropyl(trimethoxysilane) or 3-chloropropyl (triethoxysilane) and 3-chloropropyl(trichlorosilane), the preferred molar ratio is from 1:0.00001 to 1:0.03. In the conversion of 3-chloropropyl(methyldimethoxysilane) or 3-chloropropyl(methyldiethoxysilane) and 3-chloropropyl (methyldichlorosilane), the preferred molar ratio is from 1:0.00001 to 1:0.045. In the reaction of 3-chloropropyl (dimethylmethoxysilane) or of 3-chloropropyl(dimethylethoxysilane) and 3-chloropropyl(dimethylchlorosilane), the molar ratio is preferably from 1:0.00001 to 1:0.09.

The (haloorganyl)alkoxysilane and (haloorganyl)halosilane may be mixed with one another in arbitrary sequence, in an arbitrary manner, at an arbitrary temperature and with arbitrary duration, and the alcohol and the alkali hydrogensulfide may then be added jointly or in succession. The (haloorganyl)halosilane, alkali hydrogensulfide and alcohol may also be mixed with one another in arbitrary sequence, in an arbitrary manner, at an arbitrary temperature and with arbitrary duration, and the (haloorganyl)alkoxysilane may then be added. Similarly, the (haloorganyl)alkoxysilane, alkali hydrogensulfide and alcohol may be mixed with one another in an arbitrary sequence, in an arbitrary manner, at an arbitrary temperature and with arbitrary duration, and the (haloorganyl)halosilane may then be added.

Alkali-metal hydrogen sulfides that may be used in the process include lithium hydrogen sulfide (LiSH), sodium hydrogen sulfide (NaSH), potassium hydrogen sulfide (KSH) and caesium hydrogen sulfide (CsSH). The molar quantity of alkali-metal hydrogen sulfide that is used may exceed the sum of the molar quantities of (haloorganyl) alkoxysilane and of (haloorganyl)halosilane by 1% to 50%, preferably by 5% to 25%, and more preferably by 5% to 15%. Quantities of alkali-metal hydrogen sulfide less than the stoichiometrically required amount may lead to an incomplete conversion. As a result, either the product may be substantially contaminated with educt, or an elaborate distillation may become necessary in order to separate educts and products from one another.

Alcohols used in the process may be primary, secondary or tertiary alcohols having from 1 to 24, preferably from 1 to 6, and more preferably from 1 to 4, carbon atoms. Examples of alcohols include methanol, ethanol, n-propanol, isopropanol, isobutanol, n-butanol dodecanol, tetradecanol, hexadecanol or octadecanol. The amount of alcohol should be at least 100 vol. %, preferably from 250 to 1000 vol. %, and more preferably from 500 to 1000 vol. %, of the silane components used.

Polar, protic, aprotic, basic or acidic additives may be added to the reaction mixture at the beginning of the reaction and/or during the reaction and/or at the end of the reaction.

The reaction can take place at temperatures of from 0 to 180° C., preferably at between 70° C. and 150° C., and more preferably at between 70° C. and 125° C. The optimum reaction temperature in terms of the yield of target product and utilisation of the reaction volume can vary depending on the structure of the (haloorganyl)alkyoxysilane that is employed, and on the structure of the alcohol that is used as solvent. In the case of reactions in methanol, for example, a reaction temperature of from 60 to 95° C. is advantageous with regard to reaction times, amount of secondary products and pressure build-up. In the case of reactions in ethanol, a reaction temperature of from 75 to 130° C. is advantageous.

The reaction may be carried out in a closed container under a protecting gas. It may be performed in corrosion-resistant or corroson-prone reaction vessels or autoclaves. The corrosion-resistant reaction vessels or autoclaves may consist of glass, Teflon, enamelled or coated steel, Hastelloy or tantalum. The amount of secondary products may be kept at less than 20 mol % as a result of the choice of reaction conditions.

Besides the desired mercaptoorganylsilane compounds, the corresponding mono-sulfanes or disulfanes may arise as by-products. Also, depending on the structure of the monomeric mercaptoorganylsilane compound, various combinations of dimeric or oligomeric siloxanes derived from products or from products with educts may be present.

One advantage of the present process is that it does not require the use of a highly toxic, gaseous substance, such as hydrogen sulfide, as a sulfur donor. Instead, alkali metal hydrogen sulfides, which are readily meterable solids (for example sodium hydrogen sulfide), are used as sulfur donors. A further advantage of the process is that the selectivity of the reaction can be increased merely by using a closed reaction vessel (autoclave or the like) and by the addition of small quantities of (haloalkyl)halosilanes. The process is capable of producing a high conversion in a short batch time and at a temperature that is easily achieved industrially.

EXAMPLES

Definitions

The quotient formed from: a) the sum of the area percentages of 3-mercaptopropyl(triethoxysilane), $(EtO)_3Si—(CH_2)_3—S—(CH_2)_3—Si(OEt)_3$ and $(EtO)_3Si—(CH_2)_3—S_2—(CH_2)_3—Si(OEt)_3$ and b) the sum of the area percentages of 3-chloropropyl(triethoxysilane), 3-mercaptopropyl(triethoxysilane), $(EtO)_3Si—(CH_2)_3—S—(CH_2)_3—Si(OEt)_3$ and $(EtO)_3Si—(CH_2)_3—S_2—(CH_2)_3—Si(OEt)_3$, is defined as the conversion in the reaction mixtures.

The quotient formed from the a) sum of the weight percentages of 3-mercaptopropyl(triethoxysilane) and $(EtO)_3Si—(CH_2)_3—S—(CH_2)_3—Si(OEt)_3$; and b) the sum of the weight percentages of 3-chloropropyl(triethoxysilane), 3-mercaptopropyl(triethoxysilane) and $(EtO)_3Si—(CH_2)_3—S—(CH_2)_3—Si(OEt)_3$, is defined as the conversion in the isolated crude product.

The quotient formed from a) the area percentages of 3-mercaptopropyl(triethoxysilane) and b) the sum of the area percentages of 3-mercaptopropyl(triethoxysilane), $(EtO)_3Si—(CH_2)_3—S—(CH_2)_3—Si(OEt)_3$ and $(EtO)_3Si—(CH_2)_3—S_2—(CH_2)_3—Si(OEt)_3$, is defined as the selectivity in the reaction mixtures.

The quotient formed from: a) the weight percentages of 3-mercaptopropyl(triethoxysilane) and b) the sum of the weight percentages of 3-mercaptopropyl(triethoxysilane) and $(EtO)_3Si—(CH_2)_3—S—(CH_2)_3—Si(OEt)$ is defined as the selectivity in the isolated crude product.

Dried NaSH is available as a commercial product, for instance from STREM/ABCR.

GC Analysis

The GC analysis of the reaction mixtures is carried out on an HP 6890 (WLD) gas chromatograph with a 30 m long DB5 column having a thickness of 0.53 mm and a film thickness of 1.5 µm. A thermal-conductivity detector is employed as detector. The temperature program that was used included the following sequences:

Starting temperature 100° C.
Initial time 1 min.
20° C./min to 280° C.
maintain 280° C. for 10 min.

The retention-times for the following components are:

| | |
|---|---|
| at 3.3 min = | $Cl—(CH_2)_3—Si(OEt)_3$ |
| at 5.7 min Si263 = | $HS—(CH_2)_3—Si(OEt)_3$ |
| at 9.0–10.5 min | various siloxane dimers derived from educt silane and product silane |
| at 11.0 min = | $(EtO)_3Si—(CH_2)_3—S—(CH_2)_3—Si(OEt)_3$ |
| at 12.4 min = | $(EtO)_3Si—(CH_2)_3—S_2—(CH_2)_3—Si(OEt)_3$ |

Comparative Example 1

Example 1 from GB 1,102,251 produces an isolated yield of 42%.

Comparative Example 2

Comparative Example 3 from U.S. Pat. No. 5,840,952 produces a yield 81%, determined by GC.

Comparative Example 3

Comparative Example 5 from U.S. Pat. No. 5,840,952 produces a yield of 40.3%, determined by GC.

Comparative Example 4

In a stainless-steel autoclave with glass insert, 50 g 3-chloropropyl(triethoxysilane) and 125 ml dry ethanol are mixed at room temperature. 11.7 g dried NaSH are added to the solution, and the autoclave is subsequently hermetically sealed. The reaction mixture is heated in the autoclave for 120 min to 100° C. and is subsequently cooled to room temperature. The GC measurement of the reaction mixture yields the following composition in area percentage (a. %):

| | |
|---|---|
| 3-chloropropyl(triethoxysilane) | 1.5 a. % |
| 3-mercaptopropyl(triethoxysilane) | 18.4 a. % |
| dimeric siloxanes derived from 3-chloropropyl(triethoxysilane) and 3-mercaptopropyl(triethoxysilane) | 0.3 a. % |
| bis(triethoxysilylpropyl)monosulfane | 3.2 a. % |
| bis(triethoxysilylpropyl)disulfane | 0.3 a. % |

The conversion amounts to 93.7%, and the selectivity amounts to 82.9%.

Comparative Example 5

In a stainless-steel autoclave with glass insert, 50 g of 3-chloropropyl(triethoxysilane) and 125 ml dry ethanol are mixed at room temperature. 11.7 g dried NaSH are added to the solution, and the autoclave is subsequently hermetically sealed. The reaction mixture is heated in the autoclave for 240 min to 90° C. and is subsequently cooled to room temperature. The GC measurement of the reaction mixture yields the following composition in area percentage (a. %):

| | |
|---|---|
| 3-chloropropyl(triethoxysilane) | 1.5 a. % |
| 3-mercaptopropyl(triethoxysilane) | 18.8 a. % |
| dimeric siloxanes derived from 3-chloropropyl(triethoxysilane) and 3-mercaptopropyl(triethoxysilane) | 0.4 a. % |
| bis(triethoxysilylpropyl)monosulfane | 2.7 a. % |
| bis(triethoxysilylpropyl)disulfane | 0.5 a. % |

The conversion amounts to 93.7%, and the selectivity amounts to 84%.

Example 1

In a stainless-steel autoclave with glass insert 50 g 3-chloropropyl(triethoxysilane), 0.5 g 3-chloropropyl(trichlorosilane) and 125 ml dry ethanol are mixed at room temperature. 13.5 g dried NaSH are added to the solution, and the autoclave is subsequently hermetically sealed. The reaction mixture is heated in the autoclave for 240 min to 90° C. and is subsequently cooled to room temperature. The GC measurement of the reaction mixture yields the following composition in area percentage (a. %):

| | |
|---|---|
| 3-chloropropyl(triethoxysilane) | 2.5 a. % |
| 3-mercaptopropyl(triethoxysilane) | 37.0 a. % |
| dimeric siloxanes derived from 3-chloropropyl(triethoxysilane) and 3-mercaptopropyl(triethoxysilane) | 2.2 a. % |
| bis(triethoxysilylpropyl)monosulfane | 1.9 a. % |
| bis(triethoxysilylpropyl)disulfane | 0.9 a. % |

The conversion amounts to 94.3%, and the selectivity amounts to 88%.

Example 2

In a stainless-steel autoclave with glass insert, 50 g 3-chloropropyl(triethoxysilane), 1.0 g 3-chloropropyl(trichlorosilane) and 125 ml dry ethanol are mixed at room temperature. 13.5 g dried NaSH are added to the solution, and the autoclave is subsequently hermetically sealed. The reaction mixture is heated in the autoclave for 120 min to 100° C. and is subsequently cooled to room temperature. The GC measurement of the reaction mixture yields the following composition in area percentage (a. %):

| | |
|---|---|
| 3-chloropropyl(triethoxysilane) | 0.9 a. % |
| 3-mercaptopropyl(triethoxysilane) | 19.6 a. % |
| dimeric siloxanes derived from 3-chloropropyl(triethoxysilane) and 3-mercaptopropyl(triethoxysilane) | 0.3 a. % |
| bis(triethoxysilylpropyl)monosulfane | 1.2 a. % |
| bis(triethoxysilylpropyl)disulfane | 0.6 a. % |

The conversion amounts to 96%, and the selectivity amounts to 90%.

Example 3

In an autoclave with double-walled glass jacket and Hastelloy C22 lid+fittings (Buechi AG) 28.6 g dried NaSH and 600 ml dry ethanol are charged at room temperature and stirred for 15 min at 50° C. 5 g of 3-chloropropyl(trichlorosilane) are added to the suspension with a pressure burette, and the suspension is stirred for a further 10 min. Via the burette, 100 g of 3-chloropropyl(triethoxysilane) and 200 ml ethanol are added to the suspension. The mixture is heated to 93–96° C., with stirring, and the temperature is maintained for 120 min. The mixture is subsequently cooled to room temperature, and a sample is withdrawn. The GC analysis of the reaction mixture yields the following composition in area percentage:

| | |
|---|---|
| 3-chloropropyl(triethoxysilane) | 0.728 |
| 3-mercaptopropyl(triethoxysilane) | 6.099 |
| $(EtO)_3Si-(CH_2)_3-S-(CH_2)_3-Si(OEt)_3$ | 0.078 |
| $(EtO)_3Si-(CH_2)_3-S_2-(CH_2)_3-Si(OEt)_3$ | 0.061 |

Based on the values stated above, the conversion amounts to 90%, and the selectivity of the reaction amounts to 98%.

The suspension obtained is filtered and the solid matter separated off is washed with 600 ml n-pentane. The solution obtained is freed from volatile constituents on a rotary evaporator at 20–600 mbar and at 80–110° C. The suspension obtained is mixed well with 200 ml pentane and stored for 13–14 h at 4–8° C. The precipitated solid matter is separated off by filtration and washed with pentane. From the clear solution that is obtained the pentane is removed with a rotary evaporator at 20–600 mbar and at 80–110° C. 99.6 g of a colourless liquid are obtained.

Analysis with GC (dodecane as internal standard) yields the following composition of the product obtained in weight percentage:

| | |
|---|---|
| 3-chloropropyl(triethoxysilane) (GC) | 9 |
| 3-mercaptopropyl(triethoxysilane) (GC) | 86.5 |
| $(EtO)_3Si-(CH_2)_3-S-(CH_2)_3-Si(OEt)_3$ (GC) | 3.3 |

Based on the values stated above, the conversion amounts to 91%, and the selectivity of the reaction amounts to 96%.

Example 4

In an autoclave with double-walled glass jacket and Hastelloy C22 lid+fittings (Buechi AG), 37.5 g of dried NaSH and 600 ml dry ethanol are charged at room temperature. The suspension is heated and stirred for 20 min at 50° C. A mixture of 100 g of 3-chloropropyl(dimethylethoxysilane) and 5 g 3-chloropropyl(dimethylchlorosilane) is added to the suspension with a pressure burette. A further 200 ml ethanol are added to the mixture, and heating to 93–96° C. is effected with stirring. The temperature is maintained for 180 minutes and the mixture is subsequently cooled to room temperature. A sample is withdrawn and is analysed by gas chromatography. The GC analysis of the reaction mixture yields the following composition in area percentage:

| | |
|---|---|
| 3-chloropropyl(dimethylethoxysilane) | 0.091 |
| 3-mercaptopropyl(dimethylethoxysilane) | 4.621 |
| $(EtO)(CH_3)_2Si-(CH_2)_3-S-(CH_2)_3-Si(CH_3)_2(OEt)$ | 0.074 |
| $(EtO)(CH_3)_2Si-(CH_2)_3-S_2-(CH_2)_3-Si(CH_3)_2(OEt)$ | 0.155 |

Based on the values stated above, the conversion amounts to 98%, and the selectivity of the reaction amounts to 95%.

Example 5

In an autoclave with double-walled glass jacket and Hastelloy C22 lid+fittings (Buechi AG), 36.2 g of dried NaSH and 800 ml dry ethanol are charged at room temperature, heated and stirred for 15 min at 50° C. A mixture of 100 g 3-chloropropyl(triethoxysilane) and 20 g of a silane mixture consisting of 3-chloropropyl(diethoxy(chloro)silane), 3-chloropropyl(ethoxy(dichloro)silane), 3-chloropropyl (trichlorosilane) and 3-chloropropyl(triethoxysilane) is added to the suspension with a pressure burette. The 20 g are withdrawn from a silane mixture that is obtained by reaction from 694.2 g 3-chloropropyl(triethoxysilane) and 350.8 g 3-chloropropyl(trichlorosilane). Via the burette, 200 ml ethanol are added in metered amounts and heated to 102–104° C. with stirring. The temperature is maintained for 180 min. The mixture is subsequently cooled to approximately 55° C., and 2.6 g formic acid in 100 ml ethanol are added in metered amounts with a pressure burette. After 15 min, a sample is withdrawn and is analysed by gas chromatography. The GC analysis of the reaction mixture yields the following composition in area percentage:

| | |
|---|---|
| 3-chloropropyl(triethoxysilane) | 0.034 |
| 3-mercaptopropyl(triethoxysilane) | 5.494 |
| $(EtO)_3Si-(CH_2)_3-S-(CH_2)_3-Si(OEt)_3$ | 0.060 |
| $(EtO)_3Si-(CH_2)_3-S_2-(CH_2)_3-Si(OEt)_3$ | 0.028 |

Based on the values stated above, the conversion amounts to >99%, and the selectivity of the reaction amounts to 98%.

The suspension obtained is filtered and the solid matter separated off is washed with 400 ml n-pentane. The solution that is obtained is freed from volatile constituents on the rotary evaporator at 20–600 mbar and at 60–80° C. The suspension obtained is mixed with 200 ml pentane and stored for 10 h at 4–8° C. The precipitated solid matter is separated off by filtration and washed with 150 ml pentane. Pentane is removed from the solution that is obtained with a rotary evaporator at 20–600 mbar and at 60–80° C. 111.2 g of a colourless liquid are obtained. Analysis with GC (using dodecane as internal standard) yields the following composition of the product obtained in weight percentage:

| | |
|---|---|
| 3-chloropropyl(triethoxysilane) (GC) | 0.6 |
| 3-mercaptopropyl(triethoxysilane) (GC) | 96.2 |
| $(EtO)_3Si-(CH_2)_3-S-(CH_2)_3-Si(OEt)_3$ (GC) | 2.1 |

Based on the values above, the conversion amounts to >99%, and the selectivity of the reaction amounts to 98%.

Example 6

In an autoclave with double-walled glass jacket and Hastelloy C22 lid+fittings (Buechi AG), 33.6 g of dried NaSH and 800 ml dry ethanol are charged at room temperature and stirred for 15 min at 50° C. A mixture of 97 g 3-chloropropyl(triethoxysilane) and 20 g of a silane mixture consisting of 3-chloropropyl(diethoxy(chloro)silane), 3-chloropropyl(ethoxy(dichloro)silane), 3-chloropropyl (trichlorosilane) and 3-chloropropyl(triethoxysilane) is added to the suspension with a burette which is operated with compressed air. The 20 g are withdrawn from a silane mixture that is obtained by reaction from 694.2 g 3-chloropropyl(triethoxysilane) and 350.8 g 3-chloropropyl(trichlorosilane). Via the burette a further 200 ml ethanol are added to the suspension. The mixture is heated to 109–110° C. with stirring, and the temperature is maintained for 240 min. The mixture is subsequently cooled to room temperature. A sample is withdrawn and is analysed by gas chromatography. The GC analysis of the reaction mixture yields the following composition in area percentage:

| | |
|---|---|
| 3-chloropropyl(triethoxysilane) | 0.148 |
| 3-mercaptopropyl(triethoxysilane) | 6.822 |
| $(EtO)_3Si-(CH_2)_3-S-(CH_2)_3-Si(OEt)_3$ | 0.085 |
| $(EtO)_3Si-(CH_2)_3-S_2-(CH_2)_3-Si(OEt)_3$ | 0.084 |

Based on the values stated above, the conversion amounts to 98%, and the selectivity of the reaction amounts to 98%.

The suspension obtained is filtered and the solid matter separated off is washed with 400 ml n-pentane. The solution obtained is freed from volatile constituents on the rotary evaporator at 20–600 mbar and at 80–110° C. The suspension obtained is mixed well with 200 ml pentane and stored for 3–4 h at 4–8° C. The precipitated solid matter is separated off by filtration and washed with pentane. The pentane is removed from the clear solution that is obtained with a rotary evaporator at 20–600 mbar and at 80–110° C. 110.3 g of a colourless liquid are obtained. The analysis with GC (using dodecane as internal standard) yields the following composition of the product obtained in weight percentage:

| | |
|---|---|
| 3-chloropropyl(triethoxysilane) (GC) | 1.7 |
| 3-mercaptopropyl(triethoxysilane) (GC) | 94.8 |
| $(EtO)_3Si-(CH_2)_3-S-(CH_2)_3-Si(OEt)_3$ (GC) | 2.4 |

Based on the values stated above, the conversion amounts to 98%, and the selectivity of the reaction amounts to 97%.

Example 7

In an autoclave with double-walled glass jacket and Hastelloy C22 lid+fittings (Buechi AG), 33.6 g dried NaSH and 800 ml dry ethanol are charged at room temperature and stirred for 15 min at 50° C. A mixture of 100 g 3-chloropropyl(triethoxysilane) and 20 g of a silane mixture consisting of 3-chloropropyl(diethoxy(chloro)silane), 3-chloropropyl(ethoxy(dichloro)silane), 3-chloropropyl (trichlorosilane) and 3-chloropropyl(triethoxysilane) is added to the suspension with a burette which is operated with compressed air. The 20 g are withdrawn from a silane mixture that is obtained by reaction from 694.2 g 3-chloropropyl(triethoxysilane) and 350.8 g 3-chloropropyl(trichlorosilane). Via the burette a further 200 ml ethanol are added to the suspension, heated to 108–111° C., and the temperature is maintained for 240 min. The mixture is subsequently cooled to room temperature, and a sample is withdrawn. The GC analysis of the reaction mixture yields the following composition in area percentage:

| 3-chloropropyl(triethoxysilane) | 0.310 |
|---|---|
| 3-mercaptopropyl(triethoxysilane) | 5.151 |
| $(EtO)_3Si—(CH_2)_3—S—(CH_2)_3—Si(OEt)_3$ | 0.097 |
| $(EtO)_3Si—(CH_2)_3—S_2—(CH_2)_3—Si(OEt)_3$ | 0.254 |

Based on the values stated above, the conversion amounts to 95%, and the selectivity of the reaction amounts to 94%.

The suspension obtained is filtered and the solid matter separated off is washed with 400 ml n-pentane. The solution obtained is freed from volatile constituents on the rotary evaporator at 20–600 mbar and at 80–110° C. The suspension obtained is mixed well with 200 ml pentane and stored for 3–4 h at 4–8° C. The precipitated solid matter is separated off by filtration and washed with pentane. The pentane is removed from the solution that is obtained with a rotary evaporator at 20–600 mbar and at 80–110° C. 113.2 g of a colourless liquid are obtained. The analysis with GC (with dodecane as internal standard) yields the following composition of the product obtained in weight percentage:

| 3-chloropropyl(triethoxysilane) (GC) | 5.1 |
|---|---|
| 3-mercaptopropyl(triethoxysilane) (GC) | 92.2 |
| $(EtO)_3Si—(CH_2)_3—S—(CH_2)_3—Si(OEt)_3$ (GC) | 2 |

Based on the values stated above, the conversion amounts to 95%, and the selectivity of the reaction amounts to 98%.

Example 8

In an autoclave with double-walled glass jacket and Hastelloy C22 lid+fittings (Buechi AG), 18.1 g of dried NaSH and 400 ml dry ethanol are charged at room temperature, heated and stirred for 15 min at 50° C. A mixture of 50 g 3-chloropropyl(triethoxysilane) and 10 g of a silane mixture consisting of 3-chloropropyl(diethoxy(chloro)silane), 3-chloropropyl(ethoxy(dichloro)silane), 3-chloropropyl (trichlorosilane) and 3-chloropropyl(triethoxysilane) is added to the suspension with a pressure burette. The 10 g are withdrawn from a silane mixture that is obtained by reaction from 694.2 g 3-chloropropyl(triethoxysilane) and 350.8 g 3-chloropropyl(trichlorosilane). Via the burette, a further 100 ml ethanol are added to the suspension. With stirring, heating is effected to 105–110° C., and the temperature is maintained for 180 min. Subsequently cooling is effected to 50° C., and 1.3 g formic acid in 50 ml ethanol is added in metered amounts with the pressure burette. The suspension is stirred for a further 15 min, and a sample is withdrawn. The GC analysis of the reaction mixture yields the following composition in area percentage:

| 3-chloropropyl(triethoxysilane) | 0.043 |
|---|---|
| 3-mercaptopropyl(triethoxysilane) | 4.908 |
| $(EtO)_3Si—(CH_2)_3—S—(CH_2)_3—Si(OEt)_3$ | 0.112 |
| $(EtO)_3Si—(CH_2)_3—S_2—(CH_2)_3—Si(OEt)_3$ | 0.033 |

Based on the values stated above, the conversion amounts to >99%, and the selectivity of the reaction amounts to 97%.

The suspension obtained is filtered, and the solid matter separated off is washed with 400 ml n-pentane. The solution obtained is freed from volatile constituents on the rotary evaporator at 20–600 mbar and at 60–80° C. The suspension obtained is mixed with 200 ml pentane and stored for 10 h at 4–8° C. The precipitated solid matter is separated off by filtration and washed with 150 ml pentane. The pentane is removed from the solution that is obtained with a rotary evaporator at 20–600 mbar and at 60–80° C. 55.6 g of a colourless liquid are obtained. Analysis with GC (dodecane as internal standard) yields the following composition of the product obtained in weight percentage:

| 3-chloropropyl(triethoxysilane) (GC) | 0.7 |
|---|---|
| 3-mercaptopropyl(triethoxysilane) (GC) | 92.5 |
| $(EtO)_3Si—(CH_2)_3—S—(CH_2)_3—Si(OEt)_3$ (GC) | 3.7 |

Based on the values stated above, the conversion amounts to >99%, and the selectivity of the reaction amounts to 96%.

Example 9

In an autoclave with double-walled glass jacket and Hastelloy C22 lid+fittings (Buechi AG), 36.2 g dried NaSH and 800 ml dry ethanol are charged at room temperature and stirred for 15 min at 30° C. A mixture of 100 g 3-chloropropyl(triethoxysilane) and 20 g of a silane mixture consisting of 3-chloropropyl(diethoxy(chloro)silane), 3-chloropropyl(ethoxy(dichloro)silane), 3-chloropropyl (trichlorosilane) and 3-chloropropyl(triethoxysilane) is added to the suspension with a pressure burette. The 20 g are withdrawn from a silane mixture that is obtained by reaction from 694.2 g 3-chloropropyl(triethoxysilane) and 350.8 g 3-chloropropyl(trichlorosilane). Via the burette, a further 200 ml ethanol are added to the suspension, heated to 102–104° C. with stirring, and the temperature is maintained for 180 min. The mixture is subsequently cooled to approximately 57° C., and 2.6 g formic acid in 100 ml ethanol are added in metered amounts with the pressure burette. Stirring is effected for a further 15 min, and a sample is withdrawn. The GC analysis of the reaction mixture yields the following composition in area percentage:

| 3-chloropropyl(triethoxysilane) | 0.036 |
|---|---|
| 3-mercaptopropyl(triethoxysilane) | 4.754 |
| $(EtO)_3Si—(CH_2)_3—S—(CH_2)_3—Si(OEt)_3$ | 0.041 |
| $(EtO)_3Si—(CH_2)_3—S_2—(CH_2)_3—Si(OEt)_3$ | 0.026 |

Based on the values stated above, the conversion amounts to >99%, and the selectivity of the reaction amounts to 98%.

The suspension obtained is filtered and the solid matter separated off is washed with 400 ml n-pentane. The solution obtained is freed from volatile constituents on the rotary evaporator at 20–600 mbar and at 60–80° C. The suspension obtained is mixed well with 200 ml pentane and stored for 10 h at 4–8° C. The precipitated solid matter is separated off by filtration and washed with 150 ml pentane. The pentane is removed from the solution that is obtained with a rotary evaporator at 20–600 mbar and at 60–80° C. 111.6 g of a colourless liquid are obtained. Analysis with GC (dodecane as internal standard) yields the following composition of the product obtained in weight percentage:

| | |
|---|---|
| 3-chloropropyl(triethoxysilane) (GC) | 0.7 |
| 3-mercaptopropyl(triethoxysilane) (GC) | 93.7 |
| (EtO)₃Si—(CH₂)₃—S—(CH₂)₃—Si(OEt)₃ (GC) | 1.7 |

Based on the values stated above, the conversion amounts to >99%, and the selectivity of the reaction amounts to 98%.

Example 10

In an autoclave with double-walled glass jacket and Hastelloy C22 lid+fittings (Buechi AG), 36.2 g of dried NaSH and 800 ml dry ethanol are charged at room temperature and stirred for 15 min at 70–73° C. A mixture of 100 g 3-chloropropyl(triethoxysilane) and 20 g of a silane mixture consisting of 3-chloropropyl(diethoxy(chloro)silane), 3-chloropropyl(ethoxy(dichloro)silane), 3-chloropropyl (trichlorosilane) and 3-chloropropyl(triethoxysilane) is added to the suspension with a pressure burette. The 20 g are withdrawn from a silane mixture that is obtained by reaction from 694.2 g 3-chloropropyl(triethoxysilane) and 350.8 g 3-chloropropyl(trichlorosilane). Via the burette a further 200 ml ethanol are added to the suspension, heated to 101–104° C., and the temperature is maintained for 180 min. The mixture is subsequently cooled to 56° C., and 2.6 g formic acid in 100 ml ethanol are added in metered amounts with a pressure burette. Stirring is effected for 15 min, and then a sample is withdrawn. GC analysis of the reaction mixture yields the following composition in area percentage:

| | |
|---|---|
| 3-chloropropyl(triethoxysilane) | 0.042 |
| 3-mercaptopropyl(triethoxysilane) | 5.572 |
| (EtO)₃Si—(CH₂)₃—S—(CH₂)₃—Si(OEt)₃ | 0.046 |
| (EtO)₃Si—(CH₂)₃—S₂—(CH₂)₃—Si(OEt)₃ | 0.022 |

Based on the values stated above, the conversion amounts to >99%, and the selectivity of the reaction amounts to >98%.

The suspension obtained is filtered and the solid matter separated off is washed with 400 ml n-pentane. The solution obtained is freed from volatile constituents on the rotary evaporator at 20–600 mbar and at 60–80° C. The suspension obtained is mixed well with 200 ml pentane and stored for 10 h at 4–8° C. The precipitated solid matter is separated off by filtration and washed with 150 ml pentane. The pentane is removed from the clear solution that is obtained with a rotary evaporator at 20–600 mbar and at 60–80° C. 111.1 g of a colourless liquid are obtained. Analysis with GC (using dodecane as internal standard) yields the following composition of the product obtained in weight percentage:

| | |
|---|---|
| 3-chloropropyl(triethoxysilane) (GC) | 0.7 |
| 3-mercaptopropyl(triethoxysilane) (GC) | 94.9 |
| (EtO)₃Si—(CH₂)₃—S—(CH₂)₃—Si(OEt)₃ (GC) | 1.7 |

Based on the values stated above, the conversion amounts to >99%, and the selectivity of the reaction amounts to 98%.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for the preparation of (mercaptoorganyl) alkoxysilanes, comprising reacting alkali-metal hydrogen-sulfide with a mixture of (haloorganyl)alkoxysilane and (haloorganyl)halosilane in an alcohol with the exclusion of air and under elevated pressure.

2. The process of claim 1, wherein said (mercaptoorganyl) alkoxysilane compound produced is of the general formula I:

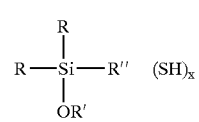

I wherein the substituents R are identical or different and are selected from the group consisting of: $C_1$–$C_8$ alkyl; $C_2$–$C_{12}$ alkenyl; $C_6$–$C_{10}$ aryl; $C_7$–$C_{16}$ aralkyl; or OR', wherein the substituents R' are identical or different and are selected from the group consisting of: a $C_1$–$C_{24}$ branched or unbranched monovalent alkyl or alkenyl group; an aryl group; and an aralkyl group;

R" is a branched or unbranched, saturated or unsaturated, aliphatic, aromatic or mixed aliphatic/aromatic divalent $C_1$–$C_{30}$ hydrocarbon group which is optionally substituted by F, Cl, Br, I, $NH_2$ or NHR'; and x is 1–3.

3. The process of claim 1, wherein said (haloorganyl) alkoxysilane compounds are of the general formula II:

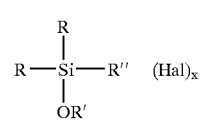

II wherein the substituents R are identical or different and are selected from the group consisting of: $C_1$–$C_8$ alkyl; $C_2$–$C_{12}$ alkenyl; $C_6$–$C_{10}$ aryl; $C_7$–$C_{16}$ aralkyl; or OR', wherein the substituents R' are identical or different and are selected from the group consisting of: a $C_1$–$C_{24}$ branched or unbranched monovalent alkyl or alkenyl group; an aryl group; and an aralkyl group;

R" is a branched or unbranched, saturated or unsaturated, aliphatic, aromatic or mixed aliphatic/aromatic divalent $C_1$–$C_{30}$ hydrocarbon group which is optionally substituted by F, Cl, Br, I, $NH_2$ or NHR';

x is 1–3; and

Hal is chlorine, bromine, fluorine or iodine.

4. The process of claim 1, wherein said (haloorganyl) halosilane compounds are of the general formula III:

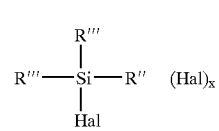

III wherein R" is a branched or unbranched, saturated or unsaturated, aliphatic, aromatic or mixed aliphatic/aromatic divalent $C_1$–$C_{30}$ hydrocarbon group which is optionally substituted by F, Cl, Br, I, $NH_2$, or NHR' wherein the substituent R' is selected from the group consisting of: a $C_1$–$C_{24}$ branched or unbranched monovalent alkyl or alkenyl group; an aryl group and an aralkyl group;

x is 1–3; and

Hal is chlorine, bromine, fluorine or iodine; and the substituents R'" are identical or different and are selected from the group consisting of: F; Cl; Br; I; $C_1$–$C_8$ alkyl; $C_2$–$C_{12}$ alkenyl; $C_6$–$C_{10}$ aryl; $C_7$–$C_{16}$ aralkyl; and OR', wherein the substituent R' is selected from the group consisting of: a $C_1$–$C_{24}$ branched or unbranched monovalent alkyl or alkenyl group; an aryl group; and an aralkyl group.

5. The process of claim 1, wherein said alkali-metal hydrogen sulfide is selected from the group consisting of: lithium hydrogen sulfide (LiSH), sodium hydrogen sulfide (NaSH), caesium hydrogen sulfide (CsSH) or potassium hydrogensulfide (KSH).

6. The process of claim 1, further comprising the addition of polar, protic, aprotic, basic or acidic additives to the reaction mixture at the beginning of the reaction and/or during the reaction and/or at the end of the reaction.

7. The process of claim 1, wherein the molar ratio of (haloorganyl)alkyoxysilane to (haloorganyl)halosilane is 1:0.00001 to 1:0.8.

8. The process of claim 1, wherein the quantity of hydrolysable Si halide in said mixture of (haloorganyl)alkyoxysilane and (haloorganyl)halosilane is between 10 mg/kg and 800 000 mg/kg.

9. The process of claim 1, wherein the molar quantity of said alkali-metal hydrogen-sulfide used in said process exceeds the sum of the molar quantities of said (haloorganyl)alkoxysilane and of said (haloorganyl)halosilane by 1% to 50%.

10. The process of claim 1, wherein said alcohol is a primary, secondary, tertiary alcohol having from 1 to 24 carbon atoms.

* * * * *